(12) United States Patent
Mohammadi

(10) Patent No.: US 8,062,674 B1
(45) Date of Patent: Nov. 22, 2011

(54) ORGANIC PESTICIDE AND METHOD OF USE

(76) Inventor: Fereidoon Mohammadi, La Crescenta, CA (US)

( * ) Notice: Subject to any disclaimer, the term of this patent is extended or adjusted under 35 U.S.C. 154(b) by 0 days.

(21) Appl. No.: 12/396,306

(22) Filed: Mar. 2, 2009

(51) Int. Cl.
*A01N 25/00* (2006.01)
(52) U.S. Cl. .......................... 424/535; 424/405; 424/725
(58) Field of Classification Search ........................ None
See application file for complete search history.

(56) References Cited

U.S. PATENT DOCUMENTS

| | | | |
|---|---|---|---|
| 3,891,571 A * | 6/1975 | Lambou et al. ................. | 516/14 |
| 6,048,565 A | 4/2000 | Getler et al. | |
| 7,927,641 B2 | 4/2011 | Harris et al. | |

OTHER PUBLICATIONS

Song (J. Dairy Sci. (2001), vol. 90, pp. 2141-2146).*

* cited by examiner

*Primary Examiner* — Susan Hoffman
(74) *Attorney, Agent, or Firm* — Lawrence S. Cohen

(57) ABSTRACT

A composition for killing insects in which the main active ingredient is whey permeate.

21 Claims, No Drawings

ORGANIC PESTICIDE AND METHOD OF USE

FIELD OF THE INVENTION

The invention is concerned with pesticides and chemicals and materials to kill pests in particular insects.

BACKGROUND

In a strict chemical sense an "organic pesticide" is one which is an organic chemical as that term is understood in chemistry. But in the present context an "organic pesticide" is one that is environmentally friendly. By this definition, few pesticides are organic. The term "natural" is also used to describe such materials and compositions.

It may be preferred to use a "natural" or "organic" pesticide when controlling pests.

Organic pesticides are usually considered as those pesticides that come from natural sources. These natural sources are usually plants, as is the case with pyrethrum (pyrethrins), rotenone or ryania (botanical insecticides), or minerals, such as boric acid, cryolite, or diatomaceous earth. Organic pesticides are largely insecticides.

Even if a product is considered to be organic, it is still a pesticide. It is important to be careful when using any pesticide, even organic or natural pesticides. Just because a product is thought to be organic, or natural, does not mean that it is not toxic. Some organic pesticides are as toxic, or even more toxic, than many synthetic chemical pesticides. Organic pesticides have specific modes of action, just as do synthetic pesticides.

To determine the relative toxicity of any pesticide to humans, check the signal word given on the pesticide label. Least toxic products carry the signal word CAUTION on their label. Products with the signal word WARNING on the label are more toxic. The most toxic pesticides have the signal word DANGER on their labels. Signal words are not an indication of the potential for environmental harm.

While some organic pesticides may be nontoxic or are only slightly toxic to people, they may be very toxic to other animals. For instance, the organic pesticide ryania is very toxic to fish. Also, some organic pesticides may be toxic to beneficial insects, such as honeybees, if they are combined with other materials, such as combining pyrethrins with rotenone.

Nature has given us plant extracts that make very effective pesticides and insect repellents. For example, some organic pest control products such as Orange Guard use a citrus-fruit peel base, such as from lemons and oranges. Citrus oils kill many flying and crawling insects on contact by destroying the waxy coating of the insect's respiratory system.

Other organic pesticides use natural extracts to repel rather than kill pests. Some products use garlic or hot peppers and essential oils of herbs such as cloves to repel insects and other pests.

The "natural" and "organic" pesticides kill with a chemical action.

DETAILED DESCRIPTION OF THE INVENTION

The present invention is an organic non-toxic composition for killing insects. It kills, not by a chemical action, but rather mechanically by a combination of mechanical effects. That is, it is understood that when an insect is in contact with the composition, it will block the breathing apparatus and will also cause the legs to stick together. First, it immobilizes the insect.

The invention is most effective on smaller insects and is gradually less effective on larger insects. For insects such asmites, insects of the ashis family, aphids, bedbugs, lice it has been found to be as nearly completely effective as observations will permit. The tests reported below provide scientific confirmation of effectiveness. The composition can be made in the form of a bulk material for application to a surface or in the form of a spray.

The primary ingredient in this invention is whey permeate.

Whey permeate has a solids content that can vary. In this invention the solids content of the weight permeate is preferably in the range of about 6% to 20%. Most preferably, the solids content is from about 12% to 14.0%.

The whey permeate may be used in its undiluted form or it may be diluted. Use of the whey permeate without dilution is very effective but is expensive. Any common diluent that will not interfere with the mechanical functions of the whey permeate on the target insects is acceptable. Commercially it is desirable to ship undiluted composition due to shipping cost, and have any dilution done by the user. Dilution has a cost benefit to the user to increase the volume of use.

With reference to the tests below, it is considered that, while 100% effectiveness is best, that is, absolute efficacy; mortality, at or above the 90% level is high and commercially acceptable efficacy. Below 90% efficacy would not be considered commercially acceptable.

As can be seen in the tests, in the undiluted form the whey permeate at either 12%, 13% or 14% solids had from absolute to high efficacy at the 24 hour level. At the 12 hour level, in some cases the efficacy was too low.

Dilution of 1:10 is has mixed efficacy at the 24 hour level. Dilution of 1:100 is not commercially acceptable.

Depending on the particular insect selected for control, at the 12 hour mortality only the undiluted form would be considered commercially effective.

Of course in a plant or adjacent soil context time is of no consequence, as the composition would normally be left in place, so the longer time is taken as the measure of effectiveness.

In the commercial distribution of the composition, in addition to the active ingredients a preservative is advisable, sodium benzoate being a preferred preservative. The preservative level should be from about ½ gram/liter to 5 grams/liter. The preferred range is from about 1 to 4 gram/liter. Sodium benzoate is a preferred preservative.

There are two specific applications for preparing the composition of the invention for use. These are:

For protection of pets or other domesticated animals; and
For protection of plants.

In the embodiment for protection of domesticated animals and livestock, the composition is preferably rendered in a spray form. An additional beneficial ingredient is Tea Tree oil, which is considered as a natural germicide, in the range of about 1 to 4 grams/liter and preferably 2 to 2.5 grams/liter.

In the embodiment for plant and surrounding soil use as spray form is also preferred. In addition, for plant use, a variant is the addition of Nettle. The Nettle is considered as a protective ingredient for farm workers who handle the plant. Nettle concentration in the composition may be in the range of about 1 to 4 grams/liter and preferably 2 to 2.5 grams/liter.

Another variant for plant use is the inclusion of liquid chlorophyll. The chlorophyll helps with plant growth. Chlorophyll concentration in the composition may be from 1 to 10 gram/liter in powder form, preferably 1 to 3 grams/liter.

The composition should have a pH of about 5 to 5.5, that is it should be slightly acidic. Normally the pH of fresh whey permeate is about 7. It is seen that the composition of ingredients will undesirably separate if the pH is more than 6. A pH of about 5.5 to 6.0 is preferred. Therefore in preparing the composition, the pH is adjusted using well known techniques.

The preferred formulation for the protection of domesticated animals and livestock is:
 a selected quantity of undiluted whey permeate with about 14% solids and pH of about 5.5; and
 about 2 grams of sodium benzoate per liter of whey permeate liquid.

Additional ingredients for the preferred formulation for domesticated animals and livestock are:
 about 1.5 grams of Tea Tree Oil per liter of whey permeate liquid.

The preferred formulation for plant protection is:
 a selected quantity of undiluted whey permeate liquid with about 14% solids and
pH of about 5.5; and
 about 2.5 grams of sodium benzoate per liter of whey permeate liquid.

Additional ingredients for the preferred formulation for plant protection are:
 about 1.6 grams of liquid chlorophyll per liter of whey permeate liquid; and
 about 2 grams of nettle per liter of whey permeate liquid Although the invention is used in a liquid form, it can be made in a powder form and later mixed with water for use. This is very important with respect to the cost of shipment as there is great economy for shipping in powder form and mixing with water at a destination. Also, the shelf life is longer for the powder form. Also, the whey permeate can be used in powder form for bedbugs. In that case the powder is distributed on the mattress or under the bed.

As is evident, the invention is not toxic or otherwise harmful to users and does not require any safety steps for its use.

Experimental Confirmation of Effectiveness

The following tests were preformed:
In the following tests:
"Sample 1" is 1 liter whey permeate with 12% solids and 1 gram of sodium benzoate.
"Sample 2" is 1 liter whey permeate with 13% solids and 2.5 grams of sodium benzoate.
"Sample 3" is 1 liter whey permeate with 14% solids and 4 grams of sodium benzoate.

The weight of 1 liter is theoretically calculated to be approximately 0.9 kg/liter. It is theoretical because it is understood that whey permeate is not normally available without solids.

Testing

Three samples (Sample 1, Sample 2 and Sample 3) were evaluated preliminarily against nymphs of the Virginiacreeper leafhopper, *Erythroneura ziczac*, adults and nymphs of the silverleaf whitefly, *Bemisia argentifolii*, nymphs of the blackmargined aphid, *Monellia caryella* and nymphs of the black pecan aphid, *Melanocallis caryaefoliae*.

Material and Methods

Materials:
 Petri dishes with lids presenting ½ inch diameter holes covered with cloth screen, to avoid plant extract condensation
 Scissors
 Adhesive tape
 Plastic and glass containers
 Fine brushes to manipulate insects
 Hand sprayers to treat insects with the plant extracts
 Dissecting microscope to observe and evaluate insect mortality
 Parafilm tape to seal Petri dishes
 Glass pipettes Methodology to Collect Insect Virginiacreeper leafhopper nymphs were collected directly from grape plants. Silverleaf whitefly nymphs and adults were collected from commercial cantaloupe and cotton plots of different locations. Blackmargined aphid and black pecan aphid nymphs were collected from pecan trees and a pecan orchard. Insects were collected by hand with fine brushes and placed in plastic bags or plastic containers. Also, crop leaves were collected to feed insects.

Methodology to Evaluate Plant Extract Treatments

In the laboratory, Petri dishes and crop leaves were washed with distilled water. In each Petri dish a corresponding crop leaf and 10 nymphs of Virginiacreeper leafhopper, blackmargined aphids and black pecan aphids were placed. In the case of the silverleaf whitefly, 10 to 20 nymphs and adults were utilized. All Petri dishes were introduced to a refrigerator at a 10° C. temperature during one to three minutes for insect inactivation.

Sample treatments were carried out manually by the use of a drop fine sprayer, covering both sides of each leaf containing insects. Each treated leaf was placed back to Petri dish, which was sealed with parafilm tape to avoid the escape of insects. Insect mortality was registered at 12 and 24 hours of application.

Treatment dates were the following: September 4 and 5 for Virginiacreeper leafhopper nymphs, September 8 for silverleaf whitefly adults, September 19 to 23 for silverleaf whitefly nymphs, September 29 to October 6 for blackmargined aphid and Oct. 8 to 14, 2008, for black pecan aphid.

Treatments evaluated were:
 1. Control (only water).
 2. Sample 1, sample 2, and sample 3 at the dilution of 1:100 (whey permeate: distilled water).
 3. Sample 1, sample 2, and sample 3 at the dilution of 1:10 (whey permeate: distilled water).
 4. Sample 1, sample 2, and sample 3 at the original concentration (100%).

Four replications of each treatment were evaluated for each insect pest.

Results

Nymphs of the Virginiacreeper Leafhopper, *Erythroneura ziczac*

Sample 1. Sample 1 extract at the original dilution (100%) presented 100% mortality of insects from 12 hours after application. The 1:10 and 1:100 dilutions had good efficacy (80.5-90.9% mortality) at 24 hours after application, but their efficacy was low (49.6-60.4% mortality) at 12 hours after application. Insect mortality in the control treatment was high (25.2-27.7%), which decreases the real mortality in the plant extract treatments (Table 1).

TABLE 1

Mortality (%) of Virginiacreeper leafhopper, *Erythroneura ziczac*, nymphs treated with three dilutions of Sample 1, at 12 and 24 hours after application.

| Treatment | Mortality (%) after 12 hr | Mortality (%) after 24 hr |
| --- | --- | --- |
| Control | 25.2 | 27.7 |
| 1:100 dilution | 49.6 | 80.5 |
| 1:10 dilution | 60.4 | 90.9 |
| Original dilution (100%) | 100 | 100 |

Sample 2. Sample 2 at the original dilution (100%) presented high efficacy (87.5-100% mortality) from 12 hours after application. The 1:10 and 1:100 dilutions had good efficacy (90.0-97.5% mortality) at 24 hours after application, but their efficacy was low (49.9-73.5% mortality) at 12 hours after application. Insect mortality in the control treatment was high (20.0-27.5%), which decreases the real mortality in the plant extract treatments (Table 2).

TABLE 2

Mortality (%) of Virginiacreeper leafhopper, *Erythroneura ziczac*, nymphs treated with three dilutions of Plant 2 extract, at 12 and 24 hours after application.

| Treatment | Mortality (%) after 12 hr | Mortality (%) after 24 hr |
| --- | --- | --- |
| Control | 20.0 | 27.5 |
| 1:100 dilution | 73.5 | 90.9 |
| 1:10 dilution | 49.9 | 97.5 |
| Original dilution (100%) | 87.5 | 100 |

Sample 3. Sample 3 at the original dilution (100%) presented high efficacy (85.6-100% mortality) from 12 hours after application. The 1:10 and 1:100 dilutions had low efficacy (17.5-48.8% mortality) at 12 and 24 hours after application (Table 3).

TABLE 3

Mortality (%) of Virginiacreeper leafhopper, *Erythroneura ziczac*, nymphs treated with three dilutions of Sample 3, at 12 and 24 hours after application.

| Treatment | Mortality (%) after 12 hr | Mortality (%) after 24 hr |
| --- | --- | --- |
| Control | 5.0 | 18.6 |
| 1:100 dilution | 17.5 | 24.6 |
| 1:10 dilution | 18.8 | 48.8 |
| Original dilution (100%) | 85.6 | 100 |

Adults of the Silverleaf Whitefly, *Bemisia argentifolii*

Sample 1. Sample 1 at the original dilution (100%) presented high efficacy (91.3-93.3% mortality) from 12 hours after application. The 1:10 and 1:00 dilutions had intermediate efficacy (67.9-92.5% mortality) at 24 hours after application and low efficacy (46.6-50.3% mortality) at 12 hours after application (Table 4).

TABLE 4

Mortality (%) of silverleaf whitefly, *Bemisia argentifolii*, adults treated with three dilutions of Sample 1, at 12 and 24 hours after application.

| Treatment | Mortality (%) after 12 hr | Mortality (%) after 24 hr |
| --- | --- | --- |
| Control | 11.1 | 18.0 |
| 1:100 dilution | 46.6 | 92.5 |
| 1:10 dilution | 50.3 | 67.9 |
| Original dilution (100%) | 91.3 | 93.3 |

Sample 2. Sample 2 at the original dilution (100%) presented intermediate efficacy (74.0% mortality) at 12 hours and high efficacy (90.0% mortality) at 24 hours after application. The 1:10 and 1:100 dilutions had high efficacy (94.4% mortality) and intermediate efficacy (85.5% mortality), respectively, at 24 hours after application. These dilutions had low efficacy (44.2-61.63%) at 12 hours after application (Table 5).

TABLE 5

Mortality (%) of silverleaf whitefly, *Bemisia argentifolii*, adults treated with three dilutions of Sample 2, at 12 and 24 hours after application.

| Treatment | Mortality (%) after 12 hr | Mortality (%) after 24 hr |
| --- | --- | --- |
| Control | 9.0 | 19.5 |
| 1:100 dilution | 61.6 | 85.5 |
| 1:10 dilution | 44.2 | 94.4 |
| Original dilution (100%) | 74.0 | 90.0 |

Sample 3. Sample 3 at the original dilution (100%) presented high efficacy (97.7% mortality) at 12 and 24 hours after application. The 1:10 dilution had intermediate efficacy (81.8% mortality) and high efficacy (95.2% mortality) at 12 and 24 hours after application, respectively. The 1:100 dilution had intermediate efficacy (65.3-82.5% mortality) (Table 6).

TABLE 6

Mortality (%) of silverleaf whitefly, *Bemisia argentifolii*, adults treated with three dilutions of Sample 3, at 12 and 24 hours after application.

| Treatment | Mortality (%) after 12 hr | Mortality (%) after 24 hr |
| --- | --- | --- |
| Control | 7.4 | 17.4 |
| 1:100 dilution | 65.3 | 82.5 |
| 1:10 dilution | 81.8 | 95.2 |
| Original dilution (100%) | 97.7 | 97.7 |

Nymphs of the Silverleaf Whitefly, *Bemisia argentifolii*

Sample 1. Sample 1 at the original dilution (100%) presented high efficacy (93.4-100% mortality) from 12 hours after application. The 1:10 and 1:100 dilutions had intermediate efficacy (71.6-79.1% mortality) at 12 hours after application and high efficacy (92.3-93.3% mortality) at 24 hours after application (Table 7).

TABLE 7

Mortality (%) of silverleaf whitefly, *Bemisia argentifolii*, nymphs treated with three dilutions of sample 1, at 12 and 24 hours after application.

| Treatment | Mortality (%) after 12 hr | Mortality (%) after 24 hr |
|---|---|---|
| Control | 2.7 | 10.8 |
| 1:100 dilution | 79.1 | 93.3 |
| 1:10 dilution | 71.6 | 92.3 |
| Original dilution (100%) | 93.4 | 100 |

Sample 2. Sample 2 at the original dilution (100%) presented high efficacy (90.8-100% mortality) from 12 hours after application. The 1:10 and 1:100 dilutions had intermediate efficacy (68.8-72.6% mortality) at 12 hours after application and high efficacy (88.2-94.4% mortality) at 24 hours after application (Table 8).

TABLE 8

Mortality (%) of silverleaf whitefly, *Bemisia argentifolii*, nymphs treated with three dilutions of Sample 2, at 12 and 24 hours after application.

| Treatment | Mortality (%) after 12 hr | Mortality (%) after 24 hr |
|---|---|---|
| Control | 3.0 | 18.9 |
| 1:100 dilution | 68.8 | 88.2 |
| 1:10 dilution | 72.6 | 94.4 |
| Original dilution (100%) | 90.8 | 100 |

Sample 3. Sample 3 at the original dilution (100%) presented intermediate efficacy (80.9% mortality) and high efficacy (99.9% mortality) at 12 and 24 hours after application, respectively. The 1:10 and 1:100 dilutions had intermediate efficacy (69.9-74.3% mortality) at 12 hours after application and high efficacy (91.1-94.6% mortality) at 24 hours after application (Table 9).

TABLE 9

Mortality (%) of silverleaf whitefly, *Bemisia argentifolii*, nymphs treated with three dilutions of Sample 3, at 12 and 24 hours after application.

| Treatment | Mortality (%) after 12 hr | Mortality (%) after 24 hr |
|---|---|---|
| Control | 4.2 | 10.2 |
| 1:100 dilution | 74.3 | 91.1 |
| 1:10 dilution | 69.9 | 94.6 |
| Original dilution (100%) | 80.9 | 99.0 |

Nymphs of the Blackmargin Aphid, *Monellia caryella*

Sample 1. Sample 1 at the original dilution (100%) presented high efficacy (86.5-96.9% mortality) from 12 hours after application. The 1:10 and 1:100 dilutions had low efficacy (39.6-52.4% mortality) at 12 hours after application and intermediate efficacy (75.0-76.4% mortality) at 24 hours after application. Insect mortality in the control treatment was high (38.3%), which decreases the real mortality in the plant extract treatments (Table 10).

TABLE 10

Mortality (%) of blackmargin aphid, *Monellia caryella*, nymphs treated with three dilutions of Sample 1, at 12 and 24 hours after application.

| Treatment | Mortality (%) after 12 hr | Mortality (%) after 24 hr |
|---|---|---|
| Control | 12.5 | 38.3 |
| 1:100 dilution | 52.4 | 75.0 |
| 1:10 dilution | 39.6 | 76.4 |
| Original dilution (100%) | 86.5 | 96.9 |

Sample 2. Sample 2 at the original dilution (100%) presented intermediate efficacy (83.1% mortality) and high efficacy (96.9% mortality) at 12 and 24 hours after application, respectively. The 1:10 and 1:100 dilutions had low efficacy (28.2-47.0% mortality) at 12 hours after application and intermediate efficacy (74.3-77.2% mortality) at 24 hours after application (Table 11).

TABLE 11

Mortality (%) of blackmargin aphid, *Monellia caryella*, nymphs treated with three dilutions of Sample 2, at 12 and 24 hours after application.

| Treatment | Mortality (%) after 12 hr | Mortality (%) after 24 hr |
|---|---|---|
| Control | 3.1 | 5.6 |
| 1:100 dilution | 28.2 | 74.3 |
| 1:10 dilution | 47.0 | 77.2 |
| Original dilution (100%) | 83.1 | 96.9 |

Sample 3. Sample 3 at the original dilution (100%) presented intermediate efficacy (83.0% mortality) and high efficacy (97.2% mortality) at 12 and 24 hours after application, respectively. The 1:10 and 1:100 dilutions had intermediate efficacy (55.0-76.6% mortality) at both evaluation times after application (Table 12).

TABLE 12

Mortality (%) of blackmargin aphid, *Monellia caryella*, nymphs treated with three dilutions of Sample 3, at 12 and 24 hours after application.

| Treatment | Mortality (%) after 12 hr | Mortality (%) after 24 hr |
|---|---|---|
| Control | 8.1 | 13.8 |
| 1:100 dilution | 55.0 | 62.5 |
| 1:10 dilution | 62.1 | 76.6 |
| Original dilution (100%) | 83.0 | 97.2 |

Nymphs of the Black Pecan Aphid, *Melanocallis caryaefoliae*

Sample 1. Sample 1 at the original dilution (100%) presented high efficacy (95.0-97.5% mortality) from 12 hours after application. The 1:10 and 1:100 dilutions had low to intermediate efficacy (41.5-83.6% mortality) at both evaluation times after application (Table 13).

TABLE 13

Mortality (%) of black pecan aphid, *Melanocallis caryaefoliae*, nymphs treated with three dilutions of Sample 1, at 12 and 24 hours after application.

| Treatment | Mortality (%) after 12 hr | Mortality (%) after 24 hr |
|---|---|---|
| Control | 8.1 | 13.1 |
| 1:100 dilution | 41.5 | 69.2 |
| 1:10 dilution | 62.2 | 83.6 |
| Original dilution (100%) | 95.0 | 97.5 |

Sample 2. Sample 2 at the original dilution (100%) presented intermediate efficacy (68.1% mortality) at 12 hours after application and high efficacy (100% mortality) at 24 hours after application. The 1:10 and 1:100 dilutions had low to intermediate efficacy (45.8-71.4% mortality) at both evaluation times after application (Table 14). Insect mortality in the control treatment was high (26.5%), which decreases the real mortality in the plant extract treatments (Table 14).

TABLE 14

Mortality (%) of blackmargin aphid, *Monellia caryella*, nymphs treated with three dilutions of Sample 2, at 12 and 24 hours after application.

| Treatment | Mortality (%) after 12 hr | Mortality (%) after 24 hr |
|---|---|---|
| Control | 2.5 | 26.5 |
| 1:100 dilution | 45.8 | 71.4 |
| 1:10 dilution | 47.2 | 69.7 |
| Original dilution (100%) | 68.1 | 100 |

Sample 3. Sample 3 at the original dilution (100%) presented intermediate efficacy (76.4% mortality) at 12 hours after application and high efficacy (97.5% mortality) at 24 hours after application. The 1:10 dilution had low efficacy (42.5% mortality) at 12 hours after application and high efficacy (90.0% mortality) at 24 hours after application. The 1:100 dilution had low efficacy (18.3-54.1% mortality) at both evaluation times after application (Table 15).

TABLE 15

Mortality (%) of blackmargin aphid, *Monellia caryella*, nymphs treated with three dilutions of Sample 3, at 12 and 24 hours after application.

| Treatment | Mortality (%) after 12 hr | Mortality (%) after 24 hr |
|---|---|---|
| Control | 10.0 | 17.5 |
| 1:100 dilution | 18.3 | 54.1 |
| 1:10 dilution | 42.5 | 90.0 |
| Original dilution (100%) | 76.4 | 97.5 |

CONCLUSIONS

1. Sample 1 at the original dilution (100%) presented a high efficacy (87-100% mortality against all insect pest species. At 1:10 and 1:100 dilutions a reduction in insect mortality was observed.
2. Sample 2 at the original dilution (100%) presented from intermediate to high efficacy (68-100% mortality) against all insect pest species. At 1:10 and 1:100 dilutions a reduction in insect mortality was observed.
3. Sample 3 at the original dilution (100%) presented from intermediate to high efficacy (76-100% mortality) against all insect pest species. At 1:10 and 1:100 dilutions a reduction in insect mortality was observed.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . "

The invention claimed is:

1. A method of killing insects comprising;
    providing an organic composition whose primary constituent is whey permeate;
    causing the composition to be exposed to insects in a manner that it will contact insects.

2. The method of claim 1 wherein the composition has a pH of 5.5 or greater.

3. The method of claim 2 wherein the composition has a pH range of 5.5 to 6.0.

4. The method of claim 2 wherein the whey permeate has a solids content of from about 10% to about 20% by weight.

5. The method of claim 4 wherein said whey permeate has a solids content of about 12% to about 14% by weight.

6. The method of claim 4 further wherein the organic composition comprises a preservative.

7. The method of claim 6 wherein the preservative comprises sodium benzoate in the range of from about ½ to 5 grams/liter.

8. The method of claim 7 wherein the sodium benzoate is in the range of from about 2 to 4 grams/liter.

9. The method of claim 8 wherein the solids content is about 12% by weight and the sodium benzoate content is about 2% by weight.

10. The method of claim 8 wherein the solids content is about 13% by weight and the sodium benzoate content is about 3% by weight.

11. The method of claim 8 wherein the solids content is about 14% by weight and the sodium benzoate content is about 4% by weight.

12. The method of claim 2 further comprising a selected amount of tea tree oil.

13. The method of claim 2 further comprising nettle in the amount of from about 0.5% to 5% by weight.

14. The method of claim 2 further comprising spraying the composition on an area for which the killing of insects in the area is desired.

15. The method of claim 2 further comprising killing insects on an animal by spraying the composition on an area of the animal.

16. The method of claim 2 further comprising applying the composition to a plant.

17. The method of claim 2 wherein the mixture consists essentially of the proportional relationship of;
1 liter of whey permeate;
1.5 grams of tea tree oil;
about 1 gram to 5 grams of sodium benzoate as a preservative.

18. A method of killing insects on plants comprising;
providing a composition comprising;
a selected amount of whey permeate having a solids content of about 14% by weight and a pH of about 5.5;
about 2.5 grams of a preservative per liter of whey permeate;
about 1.6 grams of chlorophyll per liter of whey permeate;
applying the composition to insects on a plant.

19. The method of claim 18 further wherein the composition comprises about 2 grams of nettle per liter of whey permeate.

20. A method of killing insects on domestic animals and livestock comprising;
providing a composition comprising;
a selected amount of whey permeate having a solids content of about 14% by weight and a pH of about 5.5;
about 2 grams of a preservative per liter of whey permeate
applying the composition to insects that are on a domestic animal or livestock.

21. The method of claim 20 further wherein the composition comprises about 1.5 grams of tea tree oil per liter of whey permeate.

\* \* \* \* \*